US00PP26745P3

(12) United States Plant Patent
Van De Pol

(10) Patent No.: US PP26,745 P3
(45) Date of Patent: May 24, 2016

(54) ROSE ROOTSTOCK NAMED 'PROTATU'

(50) Latin Name: *Rosa hybrida*
Varietal Denomination: Protatu

(71) Applicant: ROSAFLOR B.V., Leimuiderbrug (NL)

(72) Inventor: Peter A. Van De Pol, Overberg (NL)

(73) Assignee: ROSAFLOR B.V., Leimuiderbrug (NL)

( * ) Notice: Subject to any disclaimer, the term of this patent is extended or adjusted under 35 U.S.C. 154(b) by 184 days.

(21) Appl. No.: 13/998,983

(22) Filed: Dec. 31, 2013

(65) Prior Publication Data

US 2014/0352007 P1 Nov. 27, 2014

(30) Foreign Application Priority Data

May 27, 2013 (QZ) ..... PBR 2013/0458

(51) Int. Cl.
*A01H 5/00* (2006.01)
*A01H 5/02* (2006.01)

(52) U.S. Cl.
USPC ..... Plt./101
CPC ..... *A01H 5/0222* (2013.01)

(58) Field of Classification Search
USPC ..... Plt./101
See application file for complete search history.

(56) References Cited

PUBLICATIONS

Floraculture International Mar. 26, 2013, Moerheim and Van de Pol breeders announce revolutionary rootstock for roses, retrieved on Aug. 17, 2015, retrieved from the Internet at <www.floraculture.eu/?p=7523> 3 pp.*

* cited by examiner

*Primary Examiner* — June Hwu
(74) *Attorney, Agent, or Firm* — Buchanan, Ingersoll & Rooney PC

(57) ABSTRACT

A new and distinct rose plant is provided which is particularly well suited for service as a rootstock for a rose scion cultivar. More specifically, when so used the scion cultivar exhibits a propensity to yield an increase in biomass and the promotion of faster bud release when compared to the results achieved when the scion cultivar is grown on its own roots or on a standard rootstock, such as 'Natal Briar'. Both higher production rates combined with improved quality in the scion variety are facilitated. The new rose plant displays an upright growth habit with vigorous growth. Small single white cup-shaped blossoms are formed having five generally heart-shaped petals. Orange reproductive organs are prominently displayed at the centers of the blossoms. Medium green leaflets with finely serrated margins and a matte upper surface are displayed.

1 Drawing Sheet

Botanical/commercial classification: *Rosa hybrida*/Rose Rootstock.

Varietal denomination: cv. Protatu.

SUMMARY OF THE INVENTION

The new variety of *Rosa hybrida* rose rootstock was created by artificial pollination during 2006 at Overberg, The Netherlands, wherein two seedling parents were crossed which previously had been studied in the hope that they would contribute the desired characteristics. The female parent (i.e., the seed parent) was the '483-27' variety (unreleased and non-patented in the United States). The male parent (i.e., the pollen parent) was the '06-999' variety (unreleased and non-patented in the United States).

The parentage of the new variety can be summarized as follows:

'483-27'×'06-999'.

The seeds resulting from the above pollination were sown and small plants were obtained which were physically and biologically different from each other. Selective study resulted in the identification of a single plant of the new variety.

It was found that the new rose plant of the present invention:

(a) displays an upright growth habit with vigorous growth,
(b) forms small single white cup-shaped blossoms having five generally heart-shaped petals with the prominent display of orange reproductive organs at the center of the blossoms,
(c) exhibits medium green leaflets with finely serrated margins having a matte upper surface, and
(d) when used as a rootstock for a rose scion variety exhibits a propensity to induce an increase in biomass and the promotion of faster bud release for the scion variety.

The new variety can be readily distinguished from its '483-27' and '06-999' parents. More specifically '483-27' is thornless and '06-999' displays red flowers unlike the new variety.

The new variety provides an advantageous rootstock for use during the production of roses, including cut roses grown under greenhouse growing conditions. When the new variety is utilized as a rootstock, the scion variety commonly grows more rapidly to yield a greater biomass (e.g., 10 percent or more) within a specified period of time. Also, a yield of cut flowers commonly takes place earlier than when a standard rootstock, such as 'Natal Briar' (non-patented in the United States) is employed. Both higher production rates and improved quality in the scion variety are made possible. This provides the grower a significant economic advantage. The degree of increase has been found to be influenced by the scion variety in question and the cultivation conditions. Also, the new rootstock may make possible an acceptable yield at lower temperatures and the use of less artificial lighting.

A particularly advantageous increase in biomass has been observed when the scion variety is the 'KORcut 0006' variety (non-patented in the United States), the 'KORsteimm' variety (U.S. Plant Pat. No. 20,700), and the 'KORcoluma' variety (U.S. Plant Pat. No. 17,047). A lesser overall biomass, and lesser stem length, commonly have been found to be exhibited when such scion varieties are grown on their own roots or on a standard 'Natal Briar' rootstock.

Filed concurrently herewith are two additional United States Plant Patent Applications directed to other distinctive new rose rootstocks developed through the plant breeding and selection research of Applicant. These are U.S. Plant patent application Ser. No. 13/998,984 entitled Rose Rootstock Named 'Pronne', and U.S. Plant patent application Ser. No. 13/998,985 entitled Rose Rootstock Named 'Protano'.

Standard DNA analysis using Simple Sequence Repeat (SSR) or microsatellites can be utilized to distinguish the new 'Protatu' cultivar from other rose varieties, including the 'Pronne' and 'Protano' varieties. The presence or absence of eight standard markers with scored alleles (i.e., RHB303, RHD221, RHE2A, RHI402, RHJ404, RHM405, RH0517, and RHP519) can be utilized and were evaluated with respect to the 'Protatu', 'Pronne', and 'Protano' varieties as reported in the TABLE 1 that follows. This determination was carried out at Stichting Nederlandse Algemene Kwaliteitsdienst Tuinbouw (Netherlands Inspection Service for Horticulture), better known as Naktuinbouw. DNA from leaf samples of each cultivar was extracted using the standard Naktuinbouw CTAB DNA isolation protocol. The generated DNA fragments (alleles) were separated by gel electrophoreses. SSR DNA profiles were generated for each variety. The generated DNA fragments (alleles) were separated by gel electrophoresis. The alleles were scored present or absent and are reported hereafter.

TABLE 1

| | Marker | | | |
|---|---|---|---|---|
| | RHB303 | RHD221 | RHE2A | RHI402 |
| 'Protatu' | H | F | D | A,E |
| 'Pronne' | H | F | B,D | A,D |
| 'Protano' | G,H | F | D | A,B |

| | Marker | | | |
|---|---|---|---|---|
| | RHJ404 | RHM405 | RHO517 | RHP519 |
| 'Protatu' | D | B,D | C,D | C,F |
| 'Pronne' | D | C,D | C,D | C |
| 'Protano' | D | C,D | C,D | C,F |

The difference between 'Protatu' and 'Pronne' is 6 of the 53 alleles. The difference between 'Protatu' and 'Protano' is 5 of the 53 alleles. See G. D. Esselink, M. J. M. Smulders, and B. Voeman, "Identification of cut rose (*Rosa hybrida*) and rootstock varieties using robust sequence tagged microstallite site markers," *Theor Appl Genet,* No. 106, Pages 277 to 286 (2003).

The new variety of the present invention has been found to undergo asexual propagation beginning in 2007 at Overberg, The Netherlands, by the rooting of stem cuttings. Asexual propagation by the above-mentioned technique has shown that the characteristics of the new variety are stable and are strictly transmissible by such asexual propagation from one generation to another. Accordingly, the new variety undergoes asexual propagation in a true-to-type manner.

The new cultivar has been named 'Protatu'. At times, "PRO-3" has been associated with this cultivar.

BRIEF DESCRIPTION OF THE PHOTOGRAPHS

The accompanying photographs show as nearly true as it is reasonably possible to make the same, in color illustrations of this character, typical specimens of the plant parts of the new variety. The rose plants of the new variety were approximately five years of age and were observed during June while growing outdoors on their own roots in sandy soil at Overberg, The Netherlands.

DETAILED BOTANICAL DESCRIPTION

Figure 1:
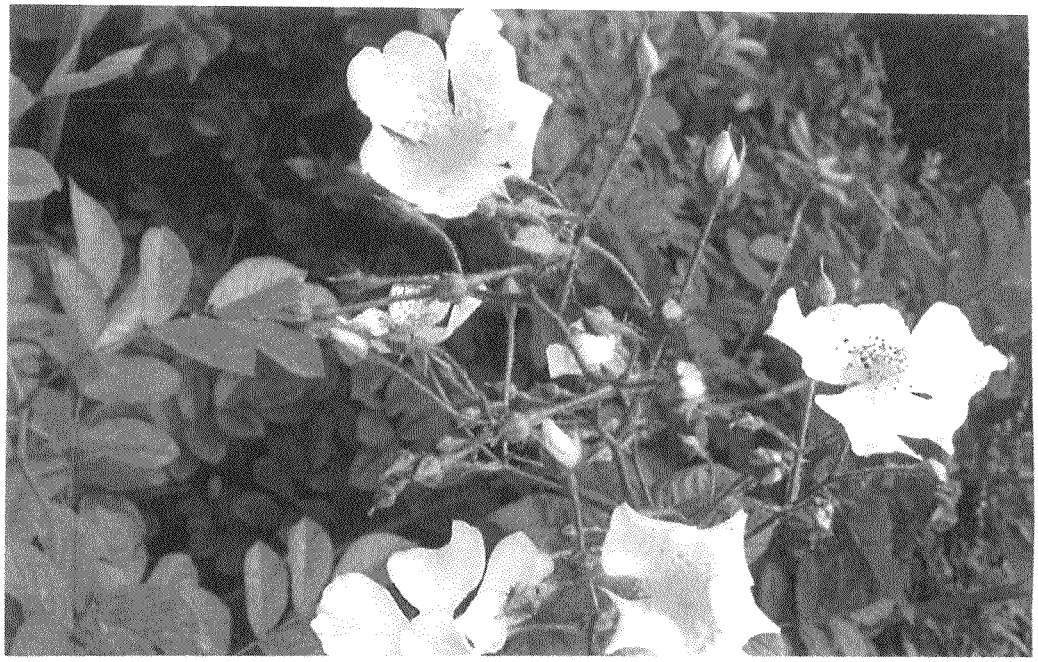
FIG. 1 illustrates typical foliage and buds and flowers of the new variety in various stages of development. The peduncles are shown to be very glandular.
Figure 2:
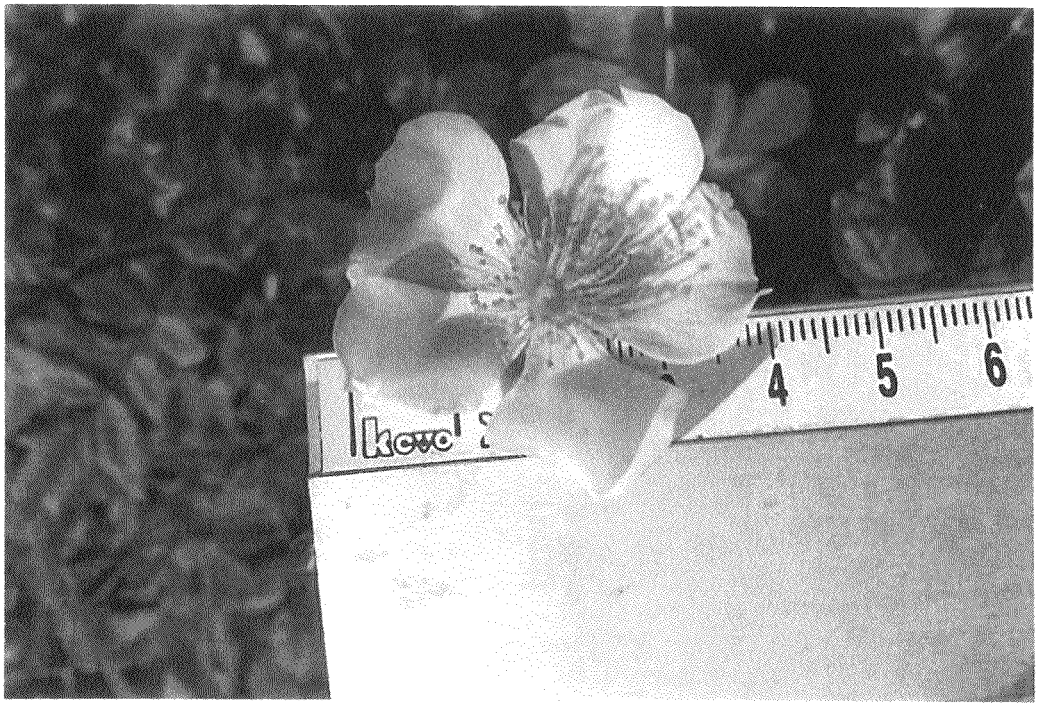
FIG. 2 illustrates a close view of a typical fully open white flower of the new cultivar wherein a profusion of orange reproductive parts is displayed at the center of the blossom. Dimensions in centimeters are included for comparative purposes.

The chart used in the identification of the colors is that of The Royal Horticultural Society (R.H.S. Colour Chart—1995 edition or equivalent). The description is based on the observation of five-year-old plants during June while growing outside in sandy soil at Overberg, The Netherlands.

Class: Most closely resembles *Rosa multiflora.*

Plant:

*Growth habit.*—Substantially upright.

*Height.*—Commonly approximately 1.75 m on average.

*Width.*—Commonly approximately 60 cm on average.

*Roots.*—Exhibits no propensity to sucker when used as rootstock, displays good compatibility with scions, provides good plant anchorage, and imparts very good vigor when used as a rootstock.

Branches:

*Internode length.*—Commonly approximately 4.8 cm on average. Such internode length renders the plant well suited for stenting as indicated hereafter.

*Thorns.*—Commonly present in a quantity of one or two per internode, and near Red Group 45A in coloration when young and mature together with some anthocyanin coloration.

*Color.*—Commonly bear slight anthocyanin coloration when young.

Foliage:

*Petioles.*—Length: approximately 11 mm on average. Diameter: approximately 1 mm on average. Texture: commonly bear a few very small thorns. Color: commonly near Red Group 45B with medium anthocyanin coloration on the upper side.

*Rachis.*—Color: Commonly near Yellow-Green Group 144A.

*Leaves.*—Length: commonly approximately 12 cm on average. Width: commonly approximately 9 cm on average.

*Leaflets.*—Number commonly 7 and 9. Shape: generally elliptical with a somewhat cuspidate tip and a cuneate base. Size: the terminal leaflets commonly are approximately 58 mm in length on average, and approximately 27 mm in width on average. Serration:

small and fine and commonly approximately 1 mm in size. Texture: with a matte upper surface. Color: commonly without anthocyanin coloration and near Yellow-Green Group 146B on the upper surface and near Yellow-Green Group 144A on the lower surface.

Inflorescence:

*Number of flowers.*—Commonly borne in clusters.

*Type.*—Single.

*Peduncle.*—Length: commonly approximately 2.5 cm on average. Diameter: commonly approximately 1 mm on average. Texture: commonly very glandular. Color: commonly near Yellow-Green Group 144B with slight anthocyanin coloration overall and strong anthocyanin coloration on glands.

*Pedicel.*—Color: commonly near Yellow-Green Group 144B with slight anthocyanin coloration overall and strong anthocyanin coloration on glands.

*Buds.*—Shape: substantially conical. Color: commonly near Yellow-Green Group 144B.

*Flower.*—Shape: cup-shaped. Diameter: small, approximately 4 cm on average. Color (in the course of opening): upper surface: near White Group 155A. under surface: near White Group 155A. Color (open flower): upper side: near White Group 155C. under side: near White Group 155C. Fragrance: none detected. Petal number: 5 under normal growing conditions. Petal shape: generally heart-shaped. Petal arrangement: slightly imbricated, and without petaloids. Stamen number: approximately 80 on average. Filaments: commonly near Yellow Group 13B in coloration. Anthers: regularly arranged around the styles, and commonly near Yellow-Orange Group 14A in coloration. Pollen: present, and orange in coloration. Pistils: connated and fused. Stigmas: commonly near Green-Yellow Group 1A in coloration. Styles: commonly near Green-Yellow Group 1A in coloration. Lastingness: commonly approximately 15 days on the plant and influenced by environmental conditions that are encountered.

*Sepals.*—Color: light colored with anthocyanin coloration that is more intense on glandular portions.

Development:

*Vegetation.*—Very strong.

*Blooming.*—Commonly commences in June extending to approximately the middle of July.

*Hardiness.*—Has well withstood −15° C. at Overberg, The Netherlands.

*Tolerance to diseases.*—Good, with no particular susceptibility to common diseases having been encountered during observations to date.

*Asexual reproduction.*—Cuttings readily undergo rooting.

*Use as understock.*—Stenting can be utilized when the new variety serves as a rose understock for a scion rose variety. In this instance, quick overall propagation can be achieved by grafting the scion variety on an unrooted cutting of the new variety. A resulting complete plant can be formed thereafter in approximately three weeks. This technique was developed by Peter A. van de Pol of Wageningen Agricultural University (The Netherlands). The word "stenting" is a contraction of the Dutch words "Stekken" (rooting of a cutting) and "Enten" (grafting). The technique and word were first published in 1979 in the Dutch *Vakblad voor de Bloemisterij*, No. 26, Pages 40 to 41, and in English in 1982, "Stenting of roses; A method for quick propagation by simultaneously cutting and grafting," *Scientia Horticulture,* No. 17, Pages 187 to 196.

The new 'Protatu' variety has not been observed under all possible environmental conditions to date. Accordingly, it is possible that the phenotypic expression may vary somewhat with changes in light intensity and duration, cultural practices, and other environmental conditions.

I claim:

1. A new and distinct rose plant characterized by the following characteristics:

(a) displays an upright growth habit with vigorous growth, (b) forms small single white cup-shaped blossoms having five generally heart-shaped petals with the prominent display of orange reproductive organs at the center of the blossoms, (c) exhibits medium green leaflets with finely serrated margins having a matte upper surface, and (d) when used as a rootstock for a cut rose scion variety exhibits a propensity to yield an increase in biomass and the promotion of faster bud release for the scion variety;

substantially as shown and described.

* * * * *